(12) United States Patent
Reuben (10) Patent No.: US 11,191,436 B2
(45) Date of Patent: Dec. 7, 2021

(54) BODY MONITORING SENSOR SYSTEM FOR USE WITH ARTICLES OF APPAREL OF KNOWN CLO INDEX TO ENSURE COMFORT UNDER EXPOSED ATMOSPHERIC CONDITIONS

(71) Applicant: Ronie Reuben, Town of Mount Royal (CA)

(72) Inventor: Ronie Reuben, Town of Mount Royal (CA)

(*) Notice: Subject to any disclaimer, the term of this patent is extended or adjusted under 35 U.S.C. 154(b) by 371 days.

(21) Appl. No.: 16/350,754

(22) Filed: Jan. 2, 2019

(65) Prior Publication Data

US 2020/0205672 A1 Jul. 2, 2020

(51) Int. Cl.
*A61B 5/01* (2006.01)
*A41D 13/005* (2006.01)
(Continued)

(52) U.S. Cl.
CPC .............. *A61B 5/01* (2013.01); *A61B 5/6804* (2013.01); *A61B 5/6805* (2013.01);
(Continued)

(58) Field of Classification Search
CPC .............. A41D 13/002; A41D 13/0025; A41D 13/005; A41D 13/0051; A41D 13/0053; A41D 13/0056; A41D 13/0058; A41D 2400/00; A41D 2400/10; A41D 2400/32; A41D 2600/00–202; A61F 2007/0233; A61F 2007/0234; A61F 2007/0236; A61F 2007/0238; A61B 5/6833; A61B 2560/0412

See application file for complete search history.

(56) References Cited

U.S. PATENT DOCUMENTS 6,080,690 A 6/2000 Lebby et al.
2018/0250159 A1* 9/2018 DeSeve, III ....... A41D 13/0051

FOREIGN PATENT DOCUMENTS

CN 108981799 A 12/2018

OTHER PUBLICATIONS

Kang, Jeongho, and Sekwang Park. "Development of comfort sensing system for human environment." Mechatronics 8.5 (1998): 459-466. (Year: 1998).*

(Continued)

*Primary Examiner* — David J. McCrosky
(74) *Attorney, Agent, or Firm* — Guy J. Houle; Houle Patent Agency Inc.

(57) ABSTRACT

A body monitoring sensor system is described and wherein a sensor module is attachable to a thermally insulated article of warmth, such as an article of apparel, having a thermal insulation of a known clo index value and wherein the sensor system has various sensors to produce various atmospheric and body condition signals to feed a computer having a processor. The processor is programmed to perform calculations to generate a output signals indicative of the corrective action required based on the protection offered by the clo index of the thermal insulation of the article of warmth and taking into account the calculated wind chill temperature and humidity as well as the wearer person's body temperature and humidity conditions to provide warmth and comfort to the user person under the actual atmospheric conditions.

20 Claims, 4 Drawing Sheets

(51) Int. Cl.
*A61B 5/00* (2006.01)
*A41D 1/02* (2006.01)
*A61F 7/02* (2006.01)

(52) U.S. Cl.
CPC .......... *A61B 5/6806* (2013.01); *A61B 5/6807* (2013.01); *A61B 5/746* (2013.01); *A41D 1/02* (2013.01); *A41D 2400/10* (2013.01); *A61B 5/0008* (2013.01); *A61B 5/6803* (2013.01); *A61B 2560/0242* (2013.01); *A61B 2560/0412* (2013.01); *A61B 2562/029* (2013.01); *A61F 2007/0233* (2013.01)

(56) References Cited

OTHER PUBLICATIONS

Schiavon, Stefano, and Kwang Ho Lee. "Dynamic predictive clothing insulation models based on outdoor air and indoor operative temperatures." Building and Environment 59 (2013): 250-260. (Year: 2013).*

* cited by examiner

BODY MONITORING SENSOR SYSTEM FOR USE WITH ARTICLES OF APPAREL OF KNOWN CLO INDEX TO ENSURE COMFORT UNDER EXPOSED ATMOSPHERIC CONDITIONS

FIELD OF THE INVENTION

The present invention relates to a body monitoring sensor system having a sensor module attachable to an outer surface of a thermally insulated article of warmth, such as an article of apparel to calculate the clo effectiveness of the article of warmth when a wearer person is subjected to actual atmospheric conditions for a predetermined period of time and when taking into account wind velocity, wind chill, ambient temperature and humidity as well as temperature and humidity against a wearer person's body, the system also provides to the user person or a guardian person, locally or remotely, information and alarm signals in the form of a display and audio and requirement for corrective action, when necessary.

DESCRIPTION OF THE PRIOR ART

Wind, temperature and humidity produce a chilling effect on a human body which could lead to serious health problems, and particularly to children not immediately surveyed by adult persons. This is particularly so in winter months where climatic conditions can be severe and change rapidly due to wind conditions and ambient temperature and humidity fluctuations producing rapidly increasing wind chill temperatures. It is important to monitor wind chill temperatures and humidity to give a better indication of what precautions need to be taken and if a person is adequately protected for exposure to such changing climatic conditions which can change quite rapidly.

People usually rely on predicted weather conditions broadcast through the media for determining what type of clothing they require to be comfortable and warm when visiting an area for all sorts of outdoor activities. For example, it is important for a person to have an indication of weather conditions in a ski area where a person speeds down ski hills and wherein abrupt wind conditions can change to seriously affect the wind chill factor subjected to the wearer person. Based on this broadcast information a person takes the decisions to wear different layers and types of clothing for themselves and their children. Because weather conditions are subject to localized and rapid variation, there is a need to be able to monitor immediately atmospheric conditions on a continuous and localized basis on site and/or remotely. There is also a need to provide immediate corrective actions to adapt to changing weather conditions to provide a person with warmth and comfort during such changing weather conditions such as during outdoor winter activities. There is a further need to inform a person that the apparel that it is wearing, or a sleeping bag, is not sufficiently insulated to keep it warm and comfortable and of health risks as well as needed corrective action, some of the corrective actions being to provide an indication of proper thermal insulation needed of its article of warmth to overcome such risks.

SUMMARY OF THE INVENTION

It is a feature of the present invention to provide a body monitoring sensor system for use in combination with an insulated article of warmth whereby to provide information to a wearer person indicative of the external weather conditions and how it can have an effect on its body covered with the thermally insulated article of warmth of a known clo index and which is presently being worn.

It is a further feature of the present invention to provide a body monitoring sensor system for use in combination with an insulated article of apparel and wherein the sensor system has a processor to provide information signals representative of actual weather conditions in the immediate area of the wearer person, and providing an information signal indicative if corrective actions is needed and to what extent the corrective action is required to maintain warmth and comfort to the wearer person.

A still further feature of the present invention to provide a body monitoring sensor system which is attachable to an outer surface of thermally insulated article of apparel and capable of producing output information signals indicative of a required clo count for the thermal insulation required based on actual external temperature conditions in the immediate vicinity of the wearer person as well as the direct effect on the user person's body and wherein the required clo count is determined taking into account a known clo count of the insulation contained in the insulated article of apparel.

Another feature of the present invention is to provide a body monitoring sensor system which is removably attachable to a thermally insulated article of apparel and capable of storing environmental weather information signals based on external temperature, wind and humidity conditions and wherein such information can be accessed remotely.

It is as still further feature of the present invention is to provide a body monitoring sensor system attached to an external surface of a thermally insulated article of warmth and capable of visually displaying environmental weather condition that a user person is subjected to and to provide corrective action for the user person to adapt to the weather conditions for the body of a wearer person to feel warm and comfortable.

Another feature of the present invention is to provide a body monitoring sensor system attached to an external surface of a thermally insulated article of apparel and capable of monitoring actual wind speed and the wind chill that the body of a person wearing the article of apparel is subjected to, and ambient temperature and humidity unaffected by the wind, internal body temperature and humidity and providing visual and/or audible signals representative thereof.

Another feature of the present invention is to provide a body monitoring sensor system attached to an external surface of an insulated article of warmth and providing an output information signal indicative of a corrective clo count for a specific thermally insulated article of warmth to which the sensor is attached and wherein the article of warmth is provided with immediate thermally insulating elements to increase or decrease its thermal insulation clo value. The article of warmth is one of an article of apparel and a sleeping bag.

According to the above mentioned features, from a broad aspect, the present invention provides a body monitoring sensor system for use in combination with an insulated article of warmth having a known clo index representative of a thermal insulation value of the article of apparel to provide warmth and comfort to a user person in predetermined environmental atmospheric conditions. The sensor system comprises a sensor module having attachment means for attachment to an outer surface of the article of warmth. The sensor module includes a wind velocity sensor, an ambient temperature sensor, a humidity sensor and a body temperature sensor for sensing temperature and humidity inside the article of warmth. The sensors generate output signals to a processor representative of actual wind velocity, ambient temperature and humidity, and temperature and humidity inside the article of apparel, respectively. The processor has a memory in which is inputted the known clo index representative of the thermal insulation value of the article of warmth. The memory has stored therein functions including formulations for calculating the actual clo index required for a wearer person to feel warm and comfortable under the actual atmospheric conditions as calculated from the output signals and including a wind chill temperature value calculation, and wherein one CLO=0.155K×m2×W−1. The computer processes the signal values and, from the inputted reference known clo index of the article of warmth, produces one or more output clo index count information signals to said wearer person whereby the user person is made aware if the article of warmth is providing suitable warmth and comfort under the actual atmospheric conditions or if the wearer person is at a health risk or will be at a health risk. The computer processor also generates an alarm information signal if the resulting clo count signal value is greater than the reference clo index of the article of warmth and if there is a need for corrective action to prevent a health risk to the user person. Preferably, but not exclusively, the article of warmth is an article of apparel, such as a jacket to maintain the body of a person warm and comfortable.

BRIEF DESCRIPTION OF THE DRAWINGS

A preferred embodiment of the present invention will now be described with reference to the accompanying drawings in which.

DESCRIPTION OF THE PREFERRED EMBODIMENT

In order for a person to feel comfortable in different atmospheric weather conditions, many factors come into play. An important factor is the thermal insulation index or value, sometimes referred to as count, of the article of apparel that the person is wearing. Another factor is the person's activity and the surrounding climatic conditions including temperature and humidity outside and inside the article of apparel reflected onto the wearer person's body. Outside weather conditions have three variables, namely, air temperature, humidity and wind speed.

Air has a low thermal conductivity but is continuously in movement. With respect to humidity, it is known that water has higher conductivity than air and therefore if a person's body sweats, such as during an activity, or outside conditions are wet and humid, the clothing and insulation will act as thermal conductors and loose some of its insulation value.

Various type of apparel wear are fabricated for use in different climatic conditions. It is important to select the proper clothing depending on climatic conditions where such article of apparel is to be worn as well as of the intended activity of the wearer person. The clo count or index associated with an article of apparel is representative of the thermal insulation value of the article of apparel and it si a measure of comfort that provides an indication of the clothing require under certain set conditions. The clo index expresses the resistance to heat transfer by clothing and serves as a comfort guide dependant on atmospheric conditions. Accordingly, clo indices vary according to seasonal clothing. For a wearer person to feel comfortable, the article of apparel must provide a thermal equilibrium with the surrounding environment.

The clo therefore provides a guide to the consumer to permit easy evaluation of the clothing required to provide comfort in various types of atmospheric climatic conditions. The following published table provides suggested limits determined by experimentation.

| Clo index | Recommended clothing |
| --- | --- |
| Greater than 2.5 | Very cold wear |
| 1.75-2.49 | Cold wear |
| 1.25-1.74 | Cool wear |
| 1.00-1.24 | Comfortable wear |
| 0.25-0.99 | Summer wear |
| Less than 0.25 | Tropical wear |

One CLO is defined as the amount of clothing required by a resting (sedentary) person to be indefinitely comfortable at ambient conditions where temperature is 21 degrees C. (70 F), relative humidity is less than 50% and wind velocity is about 0.9 kilometers/hour (approx. 20 ft/minute/hour), and wherein "K" is the wind chill, "m" is the wind speed and "W" is the heat load on the human body.

Wind chill is a factor on the human body that can produce adverse and rapid effects. It is an indicator of the sensation of cold. To maintain thermal equilibrium the amount of heat loss through clothing must not exceed the heat generated by a wearer person's body. Therefore, a wearer person should have knowledge of the thermal insulation value of the article of apparel to be worn when planning to be exposed to known atmospheric conditions including possible windchills whereby immediate corrective action can be planned in advance to eliminate the risk of frost bite and other adverse effects to the human body. The clo index of an article of apparel is therefore a very important factor when calculating weather stress on a person's body. The present invention provides a body monitoring sensor system having a sensor module attachable to an outer surface of a thermally insulated article of apparel to calculate the clo effectiveness of the article of apparel when a wearer person is subjected to actual atmospheric conditions for a predetermined period of time and when taking into account wind velocity, wind chill, ambient temperature and humidity as well as temperature and humidity against a wearer person's body. The system also provides to the user person or a guardian person, locally or remotely, information and alarm signals in the form of a display and audio and requirement for corrective action, when necessary.

Figure 5:
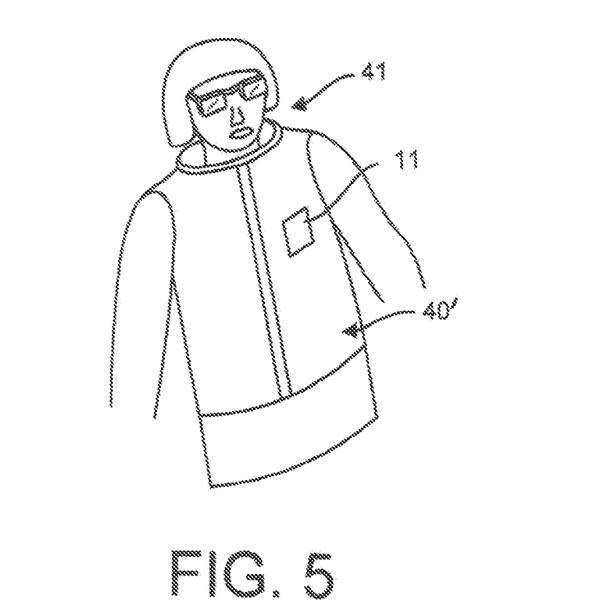
FIG. 5 is a perspective view of a wearer person equipped with an insulated article of apparel to which is attached the sensor system of the present invention.

Referring now to the drawings and more particularly to FIGS. 1 to 3 and 5, there is shown the body monitoring sensor system 10 of the present invention configured as a patch 11 which in this example has a circumferential seam allowance area 12 for permanent attachment, such as by stitching 13, to an outer surface area of an outer fabric 14 of a thermally insulated article of apparel 40', as shown in FIG. 5. The sensor system 10 is in the form of a module 15 which includes a wind velocity sensor 16 exposed to the elements, an ambient temperature sensor 17 and humidity sensor 18, both of which are exposed to the elements but shielded from the wind by a covering material 19 of predetermined rigidity, such as a thin rigid sheet of material capable of shielding the wind from the sensors 17 and 18 while permitting exposure to the environmental climatic conditions. In the embodiment illustrated in FIG. 1 an audible and visual section 20 is also provided to generate a display on a screen 20' and producing an audible signal through a speaker 20" and/or a visual signal display through a reflective background material 20''' of the section 20.

Figure 1:
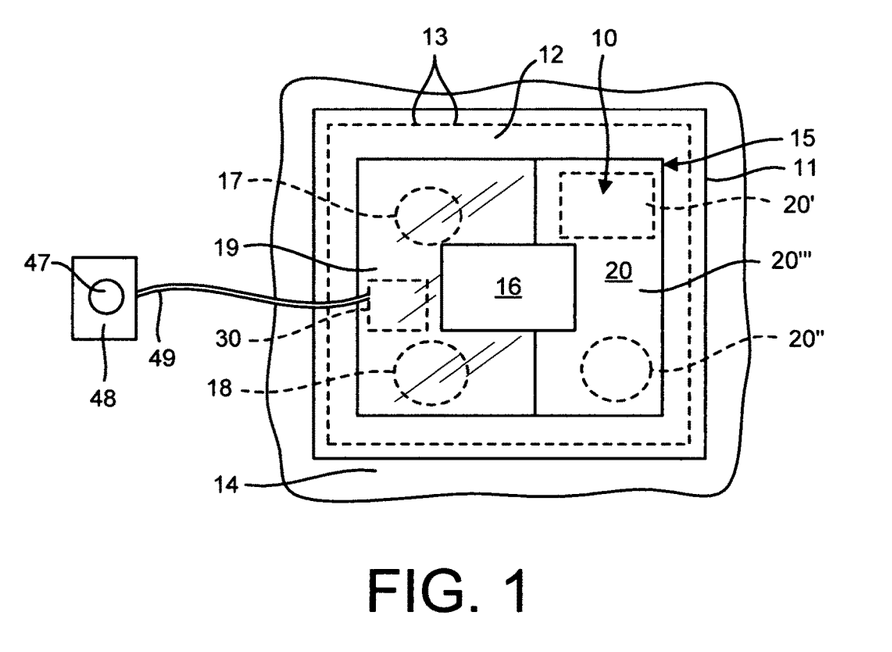
FIG. 1 is a front view of an embodiment of the body monitoring sensor module constructed in accordance with the present invention and secured to a patch to be attached to an outer surface of a thermally insulated article of apparel and showing a wind sensing section, ambient temperature and humidity sensing sections shielded from the wind, as well as a temperature and humidity sensor protected from the elements of local weather conditions and located inside the article of apparel facing a wearer person.
Figure 2:
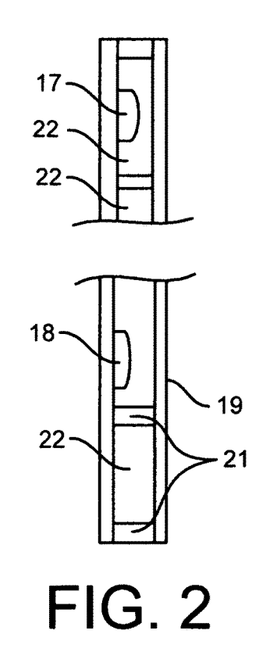
FIG. 2 is a fragmented side view showing an example of the construction of the ambient temperature and humidity sensors shielded from the wind.
Figure 3:
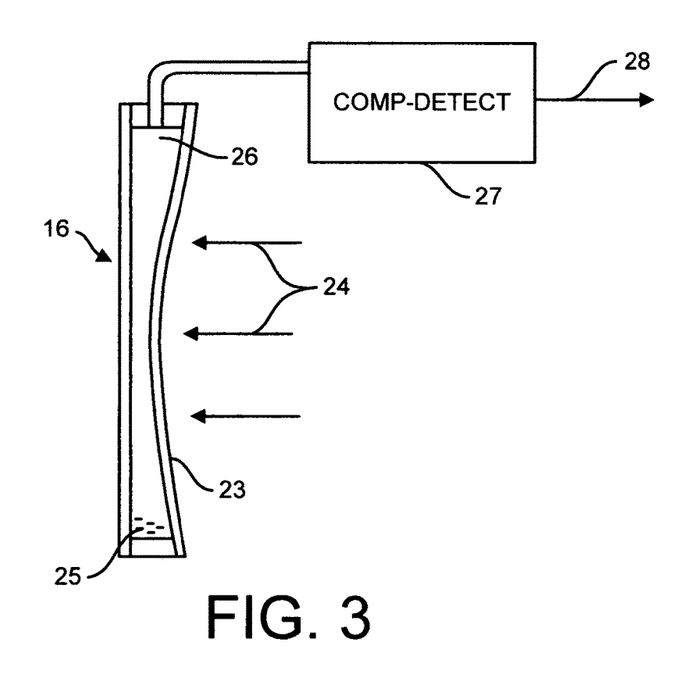
FIG. 3 is a simplified side view illustrating the construction of an embodiment of the wind sensor.

As shown in FIG. 2 the sensors 17 and 18 are supported in a structure wherein the covering material 19 is supported by spacers 21 spaced above the sensors and providing side entry ports 22 to the space surrounding the sensors 17 and 18. The sensors 17 and 18 generated output signals 17' and 18' representative of actual sensed ambient temperature and humidity. As shown in FIG. 3, the wind sensor 16 is a pressure sensor having a diaphragm 23 which when impacted by wind velocity, as represented by arrows 24, will displace to compress a fluid 25 housed in a chamber 26 which is in communication with a pressure detector means 27 calibrated to convert the fluid displacement into an output information signal 28 representative of wind speed. It is also envisaged that the displacement of the diaphragm can be measured by other means, such as the force exerted on the diaphragm or light beams measuring the displacement.

Figure 4:
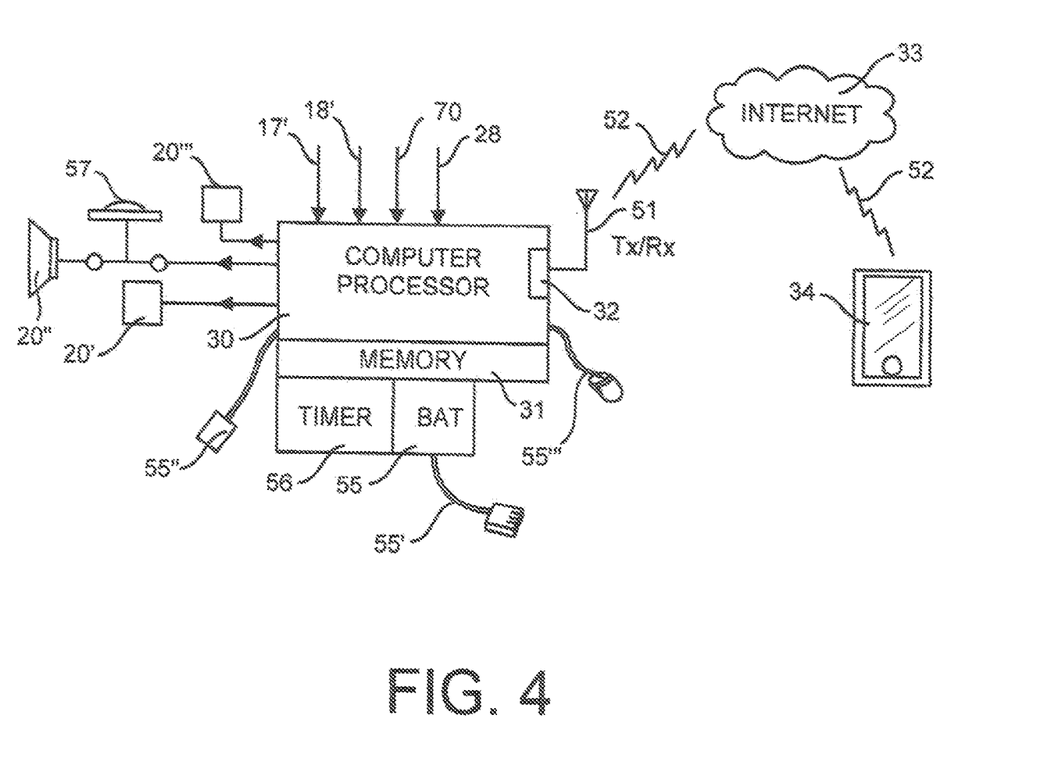
FIG. 4 is a block diagram showing schematically the processor of the computer and associated parts and different input connections and output display and means of access or transmission of its data representative of the output clo information signals and stored data calculated by the processor.
Figure 7:
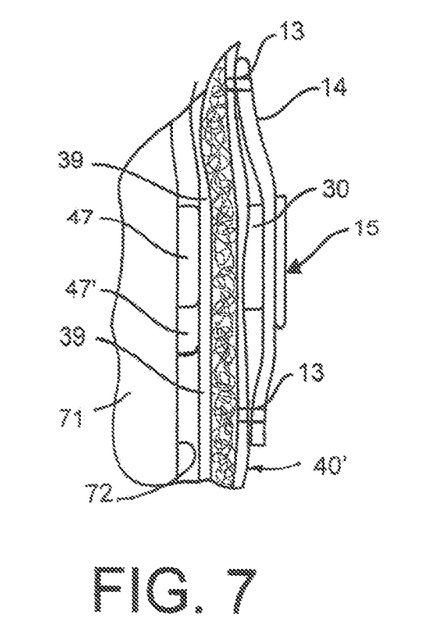
FIG. 7 is a fragmented sectional view showing an internal body temperature and humidity sensors secured to an inner lining of the insulated article of apparel and its connection to the processor attached to the rear surface of the sensor patch.

As illustrated in FIG. 4, the system 10 includes a computer controller processor 30 which may be integrated with the patch 11, such as attached to the back side of the patch 11, as shown in FIG. 7, or may be provided as a separate part secured behind the outer fabric 14 of the article of apparel 40', as shown in FIG. 5. The processor 30 has a memory 31 in which is stored functions including formulations for calculating the actual clo index required for a person to feel warm and comfortable under actual weather conditions and comparing the actual clo count calculated to a reference known clo index representative of the thermal insulation of the article of apparel and producing an output co information signal, on a continuous basis, which it stores in its memory 31, for access by the user person 41 to determine if the article of apparel 40' being worn is suitable to provide comfort under the actual weather conditions and what the actual clo index count is recommended for a person to feel comfortable exposed to the actual atmospheric weather conditions.

In the memory to the computer processor 30 there is inputted the actual clo index count (thermal insulation value) of the article of apparel, and this index is normally printed on a label attached to the article of apparel. This value is factored in a formula stored in the memory 31 of the processor 30 of the computer. The calculated actual clo index is dependent on all of the sensor signals values fed to the processor which are used in its formula and compared to the inputted reference clo index of the article of apparel to generated one or more output information signals to the user person.

As also shown in FIG. 4, the processor 30 may also receive an information signal 70 from a remote location, such as a weather station or weather television channel monitoring actual temperature and humidity and the calculated wind chill factor. For this purpose, it is equipped with a transceiver circuit 32 to transmit and receive, by means of an antenna 51. wireless information either directly or through the internet 33 by the use of an iphone 34 or other suitable devices provided with an application to access stored information in the memory 31 of the processor 30. The system is also provided with a USB port 55" and a iphone connector 55''' to access information from the memory 31 of the computer 30 and to program the memory. A communication link may also be established using the GPS system wherein the location of the wearer person is identified to the wearer person or a remote monitoring person such as a guardian person of a first responder person in the event of emergency. A charging cable 55' is also provided to charge the battery 55

The sensor module 15 may be attached to the outer surface 14 of the article of an apparel by various means, such as for example by a glue patch or VELCRO, registered trademark representative of loops and hooks removable attachments, not shown but obvious to a person skilled in the art. The sensor system 10 of the present invention may also be conveniently attached to an article of apparel having removable and interchangeable insulating panels as described in my US co-pending application Ser. No. 15/530, 362 filed on Jan. 3, 2017 and entitled Article of Warmth with Inner Replaceable Thermally Insulating Panels. The required calculated clo index can be used to generate an output clo information signal would therefore permit a user person to increase or decrease the known clo count insulation value by removing insulation panels or adding insulation panels to adapt the clo value of its insulation to that recommended by the processor output clo information signal to adapt the article of apparel to existing weather conditions for the comfort of the user person. The insulation panels described in that application have a homogeneous down feather core.

Figure 8:
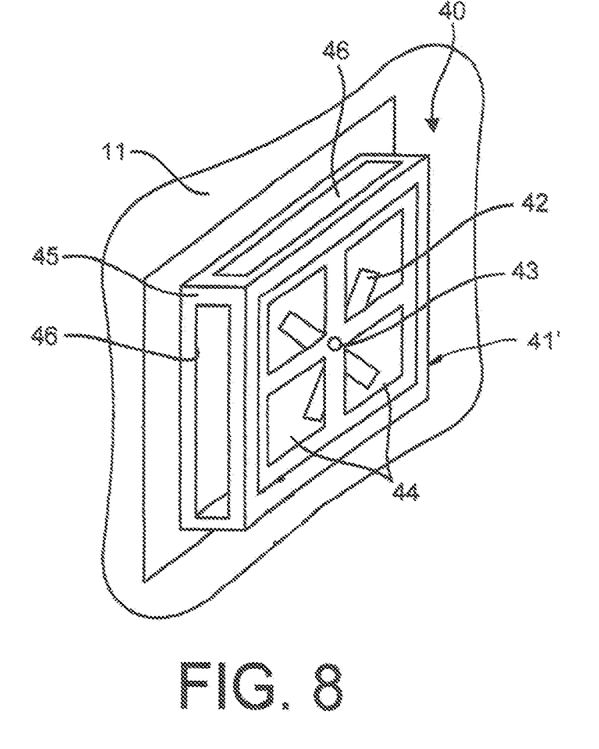
FIG. 8 is a perspective illustration of another embodiment of the wind speed sensor, herein in the form of a miniature fan secured in an open ended housing which is attached to the outer surface of the parch.

With reference now to FIG. 8 there is illustrated another embodiment of the construction of the wind sensor, herein in the form of a wind sensing miniature fan assembly 40. The assembly 40 is comprised of a housing 41' formed of rigid plastics material of suitable shape, herein illustrated as rectangular but could also be circular or other shape and in which there is mounted a miniature fan 42 supported on a rod 43 and very sensitive to air displacement. The front of the housing is provided with large openings 44 to expose the fan to frontal wind. To sense the wind, it is essential that the wind can flow through the housing and for this purpose the circumferential side wall 45 of the housing is also provided with large side opening 46. The side openings 46 can also admit wind from the side of the housing. Therefore, the wind can flow through the housing from the front or all sides of the housing. Suitable detection circuits produce a signal representative of the speed of rotation of the blades of the fan 42 to input the processor 30. The housing is glued or otherwise attached to a backing fabric or sheet material for securement to the patch 11.

Figure 6:
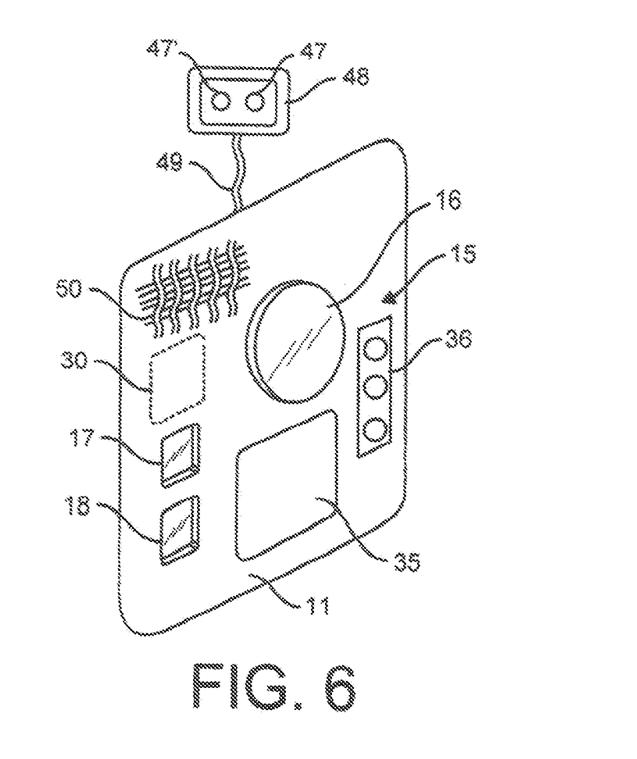
FIG. 6 is a front view similar to FIG. 1 showing a modification to the sensor patch.

As shown in FIG. 6, the sensor module 15 may be configured differently and include a display panel section 35 to display digital or analog information for visual access by other persons accompanying the wearer person to monitor the detected information and the wellbeing of the wearer, such as a child accompanied by a guardian person. A further visual display area 36 may be provided to display a color light signal representative of the output clo information signal, such as green light representative of comfort in the local temperature conditions. red indicative of alarming local temperature conditions, and yellow intermediate conditions, etc., and disposed such as to reflect its light to be visible to the wearer person. As herein shown, a temperature sensor 47 and humidity sensor 47' is connected to the patch by a wire 49 to supply internal temperature and humidity signals to the processor 30. The sensor 47 is secured to a patch 48 which can be sewn to an inner lining 39, shown in FIG. 7, of the article of apparel 40' and which faces in the direction of the body 71 of the wearer person. The the patch 48 and sensor may also be placed directly against the skin of a wearer person and retained by a suitable removable adhesive to the skin or to an under garment which is against the skin and for this purpose the wire 49 may be of suitable length to provide for such. The humidity sensor 47' senses internal humidity cause by sweat from the wearer person's body. Wind chill has a greater impact on a person's body when combined with temperature and humidity and such is taken into account by the processor when calculation its output information signals. As also shown in FIG. 6, the patch 11 may be constructed of woven fiber material in which some of the fibers, herein fibers 50, being metal strands secured such as to provide an antenna 51 for transmitting and receiving the communication signals 52, as shown in FIG. 4.

As also shown in FIG. 4, a small battery 55 is provided to power the computer and other devices requiring dc power. Also, the alarm speaker 20" can be shut-off by a push button switch 57 accessible to the user on the patch 11. A timer circuits 56 is obviously associated with the processor 30. The patch and its associated devices is also produced in as decorative assembly to provide an aesthetic appearance when secured on a thermally insulated article of apparel, such as 40' in FIG. 5.

Figure 9:
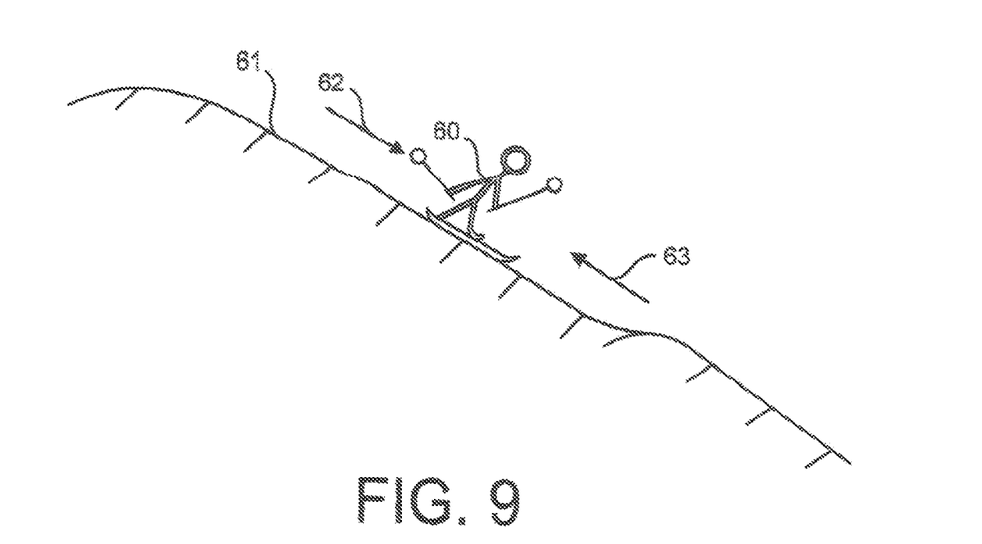
FIG. 9 is a simplified schematic view showing a use of the sensor system, herein attached a ski jacket of a wearer person, and further showing the effects of the wind onto the wearer person during ski activities.

There are many applications for the body monitoring sensor system of the present invention and one of which is to monitor local weather conditions exposed to children in ski areas wherein the children are dispersed on various ski hills away from their parents or guardian. Such is illustrated in FIG. 9. Has herein shown, when a person 60 is skiing down a hill 61 the speed of the person, depicted by arrow 62, creates an air displacement force against the wind detector indicative of wind velocity to which the wearer person is exposed to. Also, if there is a frontal wind, as indicated by arrow 63, this frontal wind adds to the air displacement force exerted on the wind detector which detects a wind velocity which is the sum of the skiers speed and the frontal wind 63 and producing a resulting wind chill factor during a predetermined period of time, which is the time of exposure as the skiing person descends down the hill 61. Of course, when the skier person reaches the bottom of the hill or faces in a different direction, this factor will change and could change drastically. Therefore, the computer will produce a signal which is comprised of different sampling signals during a predetermined period of time in which there could be drastic variations of wind speed signals as the exposure time is not constant during the wearer person's activity. The body monitoring sensor system of the present invention therefore provides to the parents or guardian a means to monitor the weather conditions to which children are exposed to prevent them from overexposure to dangerous wind chill if their ski jacket does not afford adequate insulating protection by the known clo index of the article of apparel. Through wireless access between the processor of the sensor worn by the children and the parent, the parent can remotely cause the processor to generate an audible and visual alarm to the children to immediately recall them to a safe area where weather conditions are not dangerous to them. Many other applications are foreseen for the sensor system of the present invention, such as its use in military applications for soldiers operating in severe winter climatic conditions to monitor their well being.

The body monitoring sensor system of the invention also provides real time data on the ground permitting a remote monitoring to predict danger and taking corrective action to prevent same. The system, as shown in FIG. 4, can also be connected through the internet 33 or other wireless communication system to first responders whereby rescue people in distress situations equipped with the system of the present invention. It may also communicate with a weather station, as previously mentioned, to receive data indicative of weather conditions forecasted in the area of the wearer person. For example, if a person is hiking in the woods, far form a town, the body monitoring sensor system can provide forecast information to the wearer person indicative of its actual situation taking into account all of the information signals processed and provide a predicted forecast to the wearer person of how long it can continue to hike under the current and projected weather conditions. This permits the wearer person to take an immediate corrective action for its safety.

There are other numerous applications of the body monitoring system of the invention such as for use by law enforcement people, hydro workers exposed to unfavourable weather conditions where power needs to be restored, the military also operating in adverse atmospheric conditions. The monitoring sensor system can also detect if the covered part of a person's body is too warm and for that reason will provide an indication of corrective action, such as the removal of clothing articles or the reduction of the thermal insulation.

It is further pointed out that the expression "article of warmth" as used herein is intended to apply to various types of thermally insulating articles to keep parts of the body of a wearer person warm and comfortable in cold climatic weather conditions. Such articles of warmth can include jackets, coats, vests, pants, gloves, headwear, footwear, hand gloves and mittens, sleeping bags, blankets and other articles of warmth where the body monitoring sensor system can provide a useful purpose.

It is within the ambit of the present invention to cover any obvious modifications of the embodiments of the invention described herein provided such modifications fall within the scope of the appended claims.

The invention claimed is:

1. A body monitoring sensor system for use in combination with thermally insulated article of warmth having a known clo index representative of a thermal insulation value of said article of warmth, said body monitoring sensor system providing comfort to wearer person in predetermined environmental atmospheric conditions, said body monitoring sensor system comprising:
a sensor module being attachable to an outer surface of said article of warmth;
said sensor module including a wind velocity sensor, an ambient temperature sensor, a humidity sensor and a body temperature and humidity sensor for sensing body temperature and humidity inside said article of warmth which represents body temperature and humidity of said wearer person,
said sensors generating output signals to a processor of a computer representative of actual wind velocity, ambient temperature, and humidity, body temperature and humidity of said wearer person, respectively;
said processor having a memory in which said known clo index representative of said thermal insulation value of said article of warmth is inputted as a reference,
said memory having stored therein functions including formulations for calculating the actual clo index required for a wearer person to feel warm and comfortable under the actual atmospheric conditions as calculated from said output signals and including a wind chill temperature value calculation derived from said wind velocity sensor, and wherein one clo index value=0.155K×m2×W−1, and wherein said processor produces a calculated output clo count index signal value which it determined from said reference clo index of said article of warmth to produce one or more output information signals to said wearer person and wherein said one or more output information signals indicates to said wearer person if said article of warmth is providing suitable warmth and comfort under said actual atmospheric conditions or if said wearer person is at a health risk or will be at a health risk in said actual atmospheric conditions,
said processor generating an alarm information signal if said calculated output clo count index signal value is greater than said reference clo index of said article of warmth indicating a need for corrective action to prevent a health risk to said wearer person.

2. The body monitoring sensor system for use in combination with a thermally insulated article of warmth as claimed in claim 1 wherein said sensor module is mounted on a patch adapted to be permanently secured to said outer surface of said article of warmth with said wind velocity sensor and said ambient temperature sensor facing outwardly of said patch.

3. The body monitoring sensor system for use in combination with a thermally insulated article of warmth as claimed in claim 1 wherein said sensor module is provided with a detachable attachment for removable connection to said outer surface of said article of warmth.

4. The body monitoring sensor system for use in combination with a thermally insulated article of warmth as claimed in claim 1 wherein said insulated article of warmth is an article of apparel or a sleeping bag provided with modifiable thermal insulation panels to permit said user person to increase or decrease the known clo index insulation value of said article of warmth to provide adjustment for warmth and comfort to said user person exposed to actual atmospheric conditions as determined by information signals generated by said processor indicative of the actual clo index required to feel warm and comfortable in said atmospheric conditions.

5. The body monitoring sensor system for use in combination with a thermally insulated article of warmth as claimed in claim 4 wherein said article of warmth is provided with accessible retention means to insert or remove insulation panels retained captive at predetermined locations between an outer fabric material and a liner material of said article of warmth.

6. The body monitoring sensor system for use in combination with a thermally insulated article of warmth as claimed in claim 5 wherein said insulation panels are down sheet panels provided with homogeneous down feather core.

7. The body monitoring sensor system for use in combination with a thermally insulated article of warmth as claimed in claim 1 wherein said processor is remotely and wirelessly connected to said sensor module and has a communication means for remote access thereto.

8. The body monitoring sensor system for use in combination with a thermally insulated article of warmth as claimed in claim 1 wherein said article of warmth is a jacket article of apparel and wherein said wind velocity sensor is a pressure sensor having a diaphragm which when impacted by air velocity will displace to compress a fluid, measurement means to measure the compression of said compressed fluid and convert said compressed fluid into said output signal representative of wind velocity.

9. The body monitoring sensor system for use in combination with a thermally insulated article of warmth as claimed in claim 1 wherein said wind velocity sensor is a miniature fan blade sensor which is displaced by air movement impinging on fan blades of said miniature fan, and means to detect a rotational speed of said fan blades, said memory having a stored function to calculate an average fan blade speed signal from a plurality of rotational speed signals over a predetermined time period and correlate said fan blade speed signals with said output signals of said ambient temperature and humidity sensor.

10. The body monitoring sensor system for use in combination with a thermally insulated article of warmth as claimed in claim 1 wherein said ambient temperature sensor and humidity sensor are housed in a compartment of said module and having an open-air communication port shielded from wind to measure actual ambient temperature and humidity shielded from wind.

11. The body monitoring sensor system for use in combination with a thermally insulated article of warmth as claimed in claim 1 wherein said processor is integrated in said module and has a visual display screen to visually display said output clo information signal to said user person and other signals indicative of corrective action to be taken by said user person.

12. The body monitoring sensor system for use in combination with a thermally insulated article of warmth as claimed in claim 11 wherein said visually displayed output information signal is converted by said processor to convert said signal to a color display on said visual display screen indicative of different conditions represented by said output information signal.

13. The body monitoring sensor system for use in combination with a thermally insulated article of warmth as claimed in claim 11 wherein a dc battery is housed in a pocket associated with said sensor module, said dc battery being removably retained in said pocket for charging, and wherein at least one USB port and connector is provided in said pocket for easy access.

14. The body monitoring sensor system for use in combination with a thermally insulated article of warmth as claimed in claim 1 wherein said article of warmth is an article of apparel, said processor is further provided with a transceiver to transmit said output clo information signal and other data to a remote receiver or to receive signals from a remote location, said sensor module being a patch for permanent securement to an outer fabric surface of said article of apparel, said parch having at least a portion thereof constructed of electrically conductive fibers connected to said transceiver to transmit and receive two way communication with a remote transceiver device.

15. The body monitoring sensor system for use in combination with a thermally insulated article of warmth as claimed in claim 14 wherein said article of warmth is an article of apparel for use by children to monitor their environmental atmospheric condition to which they are exposed, said remote receiver being accessible by a guardian person for remote monitoring of said output information signal representative of said environmental weather condition and need for corrective action to prevent said children to be subjected to dangerous atmospheric conditions.

16. The body monitoring sensor system for use in combination with a thermally insulated article of warmth as claimed in claim 1 wherein at least said output clo information signal stored in said memory of said processor is remotely accessible by wireless transmission by a remote wireless device.

17. The body monitoring sensor system for use in combination with a thermally insulated article of warmth as claimed in claim 16 wherein said remote wireless receiver device is an iphone having an application configured to access said output information signal as well as other stored data representative of said actual wind velocity, ambient temperature and humidity and wind velocity, exposed ambient temperature and wind chill factor data stored in said memory of said processor.

18. The body monitoring sensor system for use in combination with a thermally insulated article of warmth as claimed in claim 1 wherein said sensor module is mounted on a fabric patch having a circumferential seam allowance area for stitching said patch onto an outer fabric area of said article of warmth.

19. The body monitoring sensor system for use in combination with a thermally insulated article of warmth as claimed in claim 1 wherein said sensor module is mounted on a patch having an inner flexible material for bonding onto an outer fabric area of said article of warmth.

20. The body monitoring sensor system for use in combination with a thermally insulated article of warmth as claimed in claim 1 wherein said article of warmth is an article of apparel.

* * * * *